(12) United States Patent
Hoffman

(10) Patent No.: US 7,545,904 B2
(45) Date of Patent: Jun. 9, 2009

(54) X-RAY DETECTOR METHODS AND APPARATUS

(75) Inventor: David Michael Hoffman, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 214 days.

(21) Appl. No.: 11/522,596

(22) Filed: Sep. 18, 2006

(65) Prior Publication Data

US 2008/0069297 A1 Mar. 20, 2008

(51) Int. Cl.
*H05G 1/60* (2006.01)

(52) U.S. Cl. .............................................. 378/19; 378/5

(58) Field of Classification Search ................... 378/19, 378/5, 114; 250/370.09–370.11
See application file for complete search history.

(56) References Cited

U.S. PATENT DOCUMENTS

| | | | | |
|---|---|---|---|---|
| 6,057,552 A | * | 5/2000 | Stettner et al. | 250/370.09 |
| 6,324,249 B1 | | 11/2001 | Fazzio | 378/22 |
| 2003/0029989 A1 | * | 2/2003 | Stettner et al. | 250/208.1 |
| 2005/0173641 A1 | * | 8/2005 | Unger et al. | 250/370.09 |
| 2007/0069142 A1 | * | 3/2007 | Moody et al. | 250/370.09 |

* cited by examiner

*Primary Examiner*—Hoon Song
(74) *Attorney, Agent, or Firm*—Fisher Patent Group, LLC; Thomas M .Fisher

(57) ABSTRACT

A method includes simultaneously collecting both x-ray count data and energy charge data from a single cell.

18 Claims, 2 Drawing Sheets

X-RAY DETECTOR METHODS AND APPARATUS

BACKGROUND OF THE INVENTION

This invention relates generally to diagnostic imaging methods and apparatus, and more particularly, to methods and apparatus that provide for an x-ray detector that simultaneously provides for x-ray counting and charge integration.

Computed tomography (CT) systems sold today almost exclusively utilize x-ray detectors that have scintillator/diode cells that operate in the signal integration mode.

It would be desires to provide an x-ray detector that simultaneously provides for x-ray counting and signal integration.

BRIEF DESCRIPTION OF THE INVENTION

In one aspect, a method includes simultaneously collecting both x-ray count data and energy charge data from a single cell.

In another aspect, apparatus is provided. The apparatus includes a detector array including a plurality of x-ray detector cells wherein a portion of each x-ray detector cell is usable to collect x-ray count data and a portion is usable to collect energy charge data.

In still another aspect, a system is provided. The system includes an x-ray source, an x-ray detector positioned to receive x-rays emitted from the source, and a computer operationally coupled to the source and the detector, the computer is configured to collect both x-ray count data and energy charge data from a single cell of the detector.

DETAILED DESCRIPTION OF THE INVENTION

There are herein described methods and apparatus useful for imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

Figure 1:
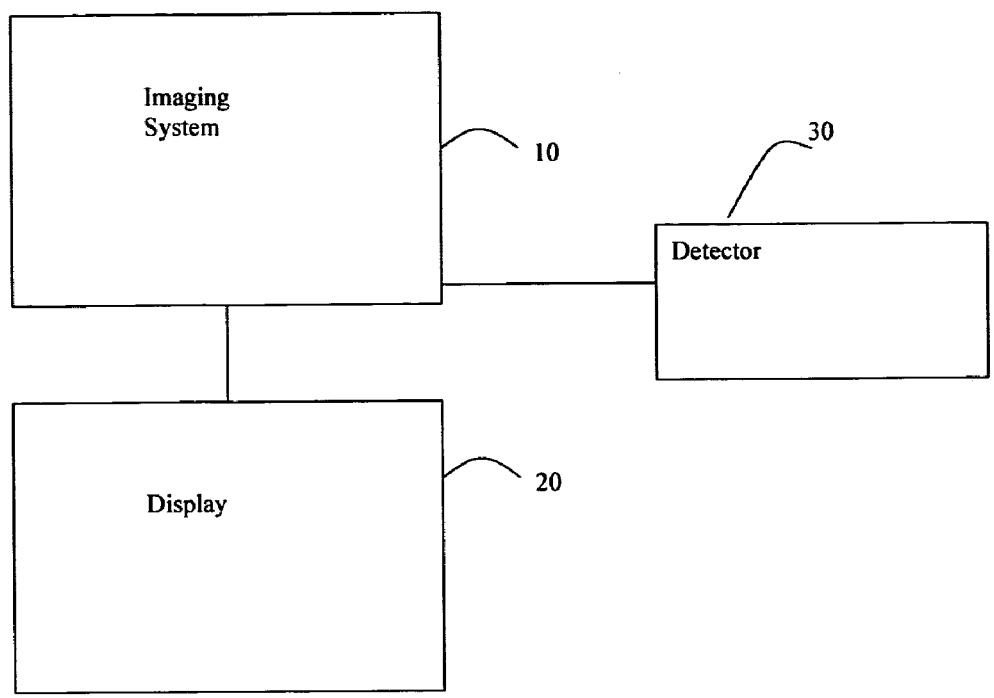
FIG. 1 illustrates an exemplary diagnostic imaging system.

FIG. 1 illustrates an imaging system 10 with an associated display 20. Imaging system 10 can be of any modality, but in one embodiment, system 10 is a CT system. In another embodiment, system 10 is a dual modality imaging system such as a combined CT/PET system and data processing can be done in one modality (e.g., CT) and the processed data can be transferred to the other modality (e.g., PET). Display 20 can be separate from system 10 or integrated with system 10. System 10 includes an acquisition device such as an x-ray radiation detector 30. X-ray detector 30 can be separate from system 10 or integrated with system 10.

The x-ray imaging system includes a processing circuit. The processing circuit (e.g., a microcontroller, microprocessor, custom ASIC, or the like) is coupled to a memory and a display device. The memory (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

The memory may also store a computer program including instructions executed by the processing circuit to implement the functions described herein. The processing circuit provides an image for display on a device. The detector may be a flat panel solid state image detector, for example, although conventional film images stored in digital form in the memory may also be processed. In one embodiment, the processing circuit executes instructions stored in firmware (not shown).

Of course, the methods described herein are not limited to practice in system 10 and can be utilized in connection with many other types and variations of imaging systems. In one embodiment, the processing circuit is a computer that is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

This disclosure describes an improvement to current detector designs that enables the simultaneous collection of x-ray counting and signal integration information. CT is moving towards a mode of counting and measuring the energy of each x-ray to enable a number of energy discrimination and tissue differentiation application advantages. These advantages have been very well enumerated in the past. One key issue is that x-rays arrive at too high a rate to effectively be counted with energy measurements at the highest flux rates. The herein described methods and apparatus are provided to at least partially solve the problem. The herein described apparatus and methods allow for an adaptive binning approach or counting at low flux rates with simultaneous energy integration information available for the higher flux rates. The herein described methods and apparatus provide for a simultaneous acquisition of both types of information. The silicon wafer of a detector cell can be fabricated into 2D sensing arrays with each sensing area or cell being designed so as to provide both counting and integration signals. The geometry of the two sub cells within each existing cell today, can be in any of a large number of configurations. Designs can include a half / half cell, two concentric rings cell design, a large area and a small area cell, a cell with an offset sensing area in one corner of an existing cell, etc. One area of the cell is made with the current photosensor design approach that operates in the integrating mode and the other portion of the cell is made as a x-ray counting configuration utilizing a conventional avalanche photodiode structure or utilizing a Si-PMT structure, both areas being rendered in the same silicon wafer and both in the same detector cell. In one embodiment, the count data is collected from approximately 80% of the cell and the energy charge data is collected from approximately 20% of the cell. In alternative embodiments, count data can be collected from approximately 70% of the cell or from approximately 90% of the cell with the remainder of the cell being used for energy charge data.

Figure 2:
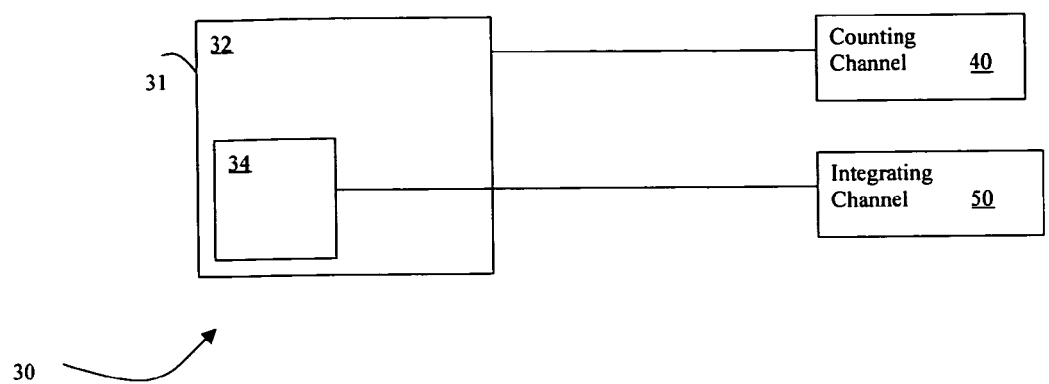
FIG. 2 illustrates one embodiment of a cell of a detector.

FIG. 2 illustrates one embodiment of a cell 31 of detector 30. The cell 31 includes a counting area or portion 32 and an integrating area or portion 34. Cell 31 may be any size but in one embodiment, cell 31 is approximately 1 mm×1 mm. During operation of the imaging system 10, detector 30 is polled or more specifically, cell 31 is polled, and there are two data outputs. There is a counting channel 40 and an integrating channel 50.

This would enable the simultaneous collection of both counting and integrating information. Later during the reconstruction process, a decision would be made on what type of information to use on a view by view basis. For example data collected from a low count rate regime can be used differently than data collected from a high count rate regime. The transition from the low count rate to the high count rate regime is in the range of 5-50 Million X-rays per mm2 per second, and is based on the achieved performance of the particular X-ray sensor counting design and performance. There are also a number of ways that these signals may be combined in a beneficial way in the reconstruction process.

Technical effects include that the herein described methods and apparatus provide an x-ray CT detector that can operate in a very high flux rate environment as is found in CT systems. This high flux rate operation is enabled by a hybrid cell design that enables the simultaneous collection of two types of information with a later decision on what type of information to use in the reconstruction process. The two types of information collected are x-ray counting with energy discrimination and x-ray energy integration. The herein described methods and apparatus enable a number of energy discrimination and tissue differentiation application advantages. These advantages have been very well enumerated in the past.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method comprising:
   collecting x-ray count data from a cell; and
   collecting energy charge data from the cell simultaneously with said collecting x-ray count data; wherein the count data is collected from a silicon photomultiplier area of the cell and the energy charge data is collected from a photodiode area of the cell.

2. A method in accordance with claim 1 further comprising retrospectively deciding which collected data to use in an image reconstruction process.

3. A method in accordance with claim 1 further comprising using both collected data in an image reconstruction process.

4. A method in accordance with claim 1 further comprising using the x-ray count data retrospectively when it is determined that the data came from a low count rate regime.

5. A method in accordance with claim 1 further comprising using the x-ray count data retrospectively when it is determined that the data came from a low count rate regime to perform tissue differentiation or material decomposition.

6. A method in accordance with claim 1 further comprising using the energy charge data retrospectively when it is determined that the data came from a high count rate regime.

7. A method in accordance with claim 1 wherein the count data is collected from approximately 80% of the cell and the energy charge data is collected from approximately 20% of the cell.

8. Apparatus comprising:
   a detector array comprising a plurality of x-ray detector cells wherein a portion of each x-ray detector cell is usable to collect x-ray count data and a portion is usable to simultaneously collect energy charge data; wherein said x-ray count data portion is about 80% of the cell and said energy charge data portion is about 20% of the cell.

9. Apparatus in accordance with claim 8 further comprising a computer operationally connected to said detector array, said computer configured to retrospectively determine if x-ray count data, and/or energy data should be used in an image reconstruction process.

10. Apparatus in accordance with claim 9 wherein said computer further configured to perform a tissue differentiation or a material decomposition on the data when the data for came from a low count rate regime.

11. Apparatus in accordance with claim 10 wherein said computer configured to use the energy charge data retrospectively when it is determined that the data came from a high count rate regime.

12. Apparatus in accordance with claim 11 wherein said x-ray count data portion comprises a silicon photomultiplier area of the cell and said energy charge portion comprises a photodiode area of the cell.

13. Apparatus in accordance with claim 8 wherein said x-ray count data portion comprises a silicon photomultiplier area of the cell and said energy charge portion comprises a photodiode area of the cell.

14. A system comprising:
   an x-ray source;
   an x-ray detector positioned to receive x-rays emitted from said source; and
   a computer operationally coupled to said source and said detector, said computer configured to simultaneously collect both x-ray count data and energy charge data from a single cell of said detector; wherein the count data is collected from a silicon photomultiplier area of the cell and the energy charge data is collected from a photodiode area of the cell.

15. A system in accordance with claim 14 wherein said computer further configured to retrospectively decide which collected data to use in an image reconstruction process.

16. A system in accordance with claim 14 wherein said computer further configured to use both collected data in an image reconstruction process.

17. A system in accordance with claim 14 wherein said computer further configured to use the x-ray count data retrospectively when it is determined that the data came from a low count rate regime.

18. A system in accordance with claim 14 wherein said computer further configured to use the x-ray count data retrospectively when it is determined that the data came from a low count rate regime to perform tissue differentiation or material decomposition.

* * * * *